United States Patent [19]
Itoi

[11] Patent Number: 5,686,655
[45] Date of Patent: Nov. 11, 1997

[54] GAS CHROMATOGRAPH/MASS SPECTROMETER SYSTEM

[75] Inventor: Hiroto Itoi, Kyoto, Japan

[73] Assignee: Shimadzu Corporation, Kyoto, Japan

[21] Appl. No.: 654,669

[22] Filed: May 29, 1996

[30] Foreign Application Priority Data

May 30, 1995 [JP] Japan ................. 7-156912

[51] Int. Cl.⁶ .................. G01N 30/72; G01N 31/08; B01D 59/44
[52] U.S. Cl. .................. 73/23.37; 73/23.42; 96/106; 96/104; 250/288; 422/89
[58] Field of Search .................. 73/23.37, 23.4, 73/23.42, 23.35; 96/106, 104; 250/288; 422/89

[56] References Cited

U.S. PATENT DOCUMENTS

| | | | |
|---|---|---|---|
| 3,128,427 | 4/1964 | Hampton | 324/33 |
| 3,291,980 | 12/1966 | Coates et al. | 250/41.9 |
| 3,471,692 | 10/1969 | Llewellyn et al. | 250/41.9 |
| 3,563,083 | 2/1971 | Benz | 73/23.1 |
| 3,566,674 | 3/1971 | Talroze et al. | 73/23.1 |
| 3,589,171 | 6/1971 | Haley | 73/23.1 |
| 5,068,533 | 11/1991 | Grossman et al. | 250/288 |
| 5,083,450 | 1/1992 | Grindstaff | 73/23.35 |
| 5,094,099 | 3/1992 | Ross | 73/23.37 |
| 5,437,179 | 8/1995 | Wiegand et al. | 73/23.35 |
| 5,467,635 | 11/1995 | Nakagawa et al. | 73/23.35 |

*Primary Examiner*—Hezron E. Williams
*Assistant Examiner*—J. David Wiggins
*Attorney, Agent, or Firm*—Oliff & Berridge

[57] ABSTRACT

Conventionally, the mass spectrometer unit is placed beside the gas chromatograph unit when the gas chromatograph unit is coupled with a mass spectrometer unit, whereas the normal detector is placed on the top of the gas chromatograph unit when it is coupled with a normal detector. This requires different structure of the gas chromatograph unit. In the gas chromatograph/mass spectrometer (GC/MS) system of the present invention that uses a suitably modified and re-designed mass spectrometer, the mass spectrometer unit is mounted on the top of the casing of the gas chromatograph unit. Thus a common gas chromatograph unit can be used whether it is coupled with a normal detector or with a mass spectrometer unit. Another advantage of the GC/MS system of the present invention is that it occupies less table-top or floor space.

8 Claims, 4 Drawing Sheets

Fig.1A
Fig.1B
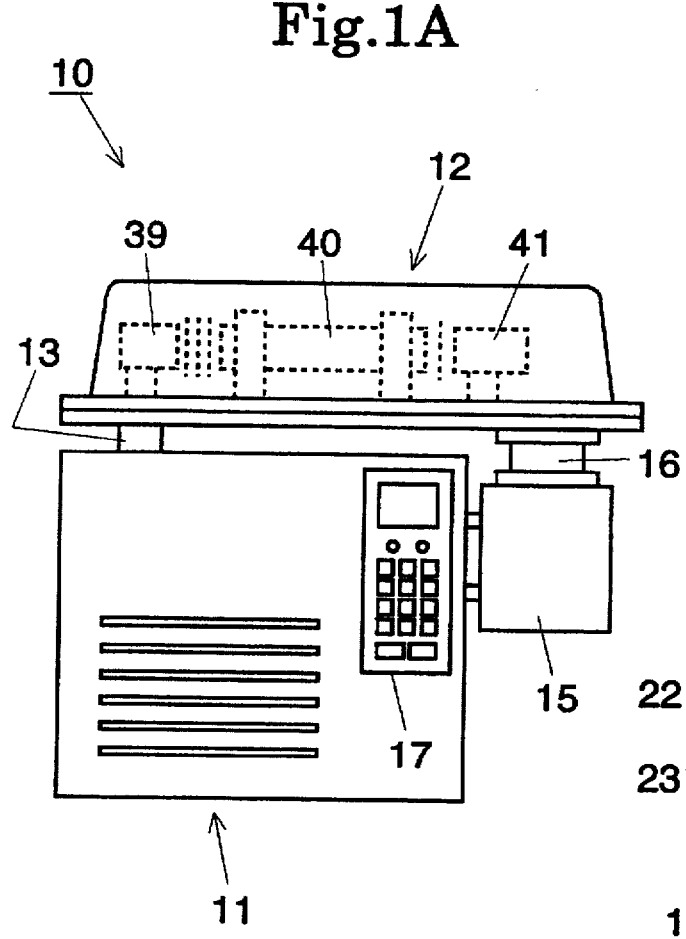
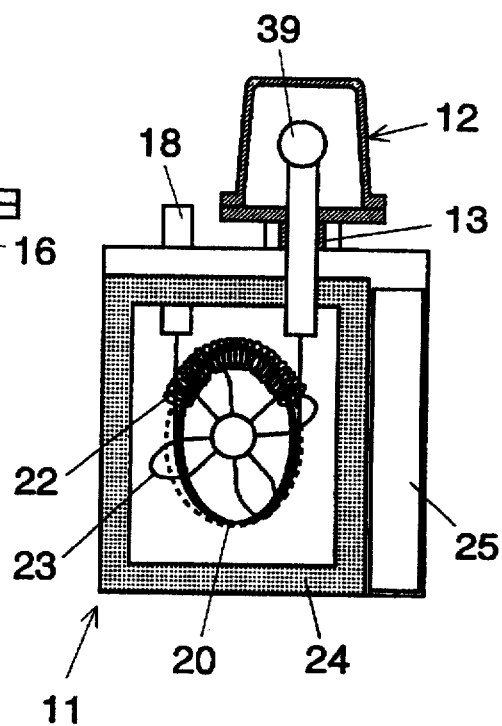

GAS CHROMATOGRAPH/MASS SPECTROMETER SYSTEM

The present invention relates to a gas chromatograph/mass spectrometer system (GC/MS).

BACKGROUND OF THE INVENTION

A detector of a gas chromatograph (GC) continuously measures a specific physical property of the gas effluent from the column and draws a chromatogram representing the change in the specific physical property. A thermal conductivity detector (TCD) or a hydrogen flame ionization detector (FID) is typically used as a detector of a gas chromatograph system. Constituents of a sample are measured qualitatively based on the time (retention time) and quantitatively based on the height (or area) of each peak in the chromatogram.

A gas chromatograph/mass spectrometer (GC/MS), on the other hand, carries out a mass spectrometric analysis for each constituent of the sample separated by the column with a mass spectrometer (MS) and thus enables highly sensitive and accurate identification of each constituent.

Since, in many cases, a gas chromatograph requires temperature control of the column, the column is placed in an oven. Thus the casing of a gas chromatograph unit is generally large enough to accommodate an oven. In a conventional gas chromatograph system that uses a normal detector such as the TCD or FID, the detector is typically mounted on the top of the casing of the gas chromatograph unit, and therefore, as shown in FIG. 5, a sample inlet 62 and a sample outlet 63 (which is to be connected to the detector) are arranged on the top of the casing 61.

A mass spectrometer unit, on the other hand, occupies a larger space than the normal detectors do. Thus, in a conventional gas chromatograph/mass spectrometer system, as shown in FIG. 3, a mass spectrometer unit 52 is placed at a side of the casing of the gas chromatograph unit 51. This requires a modification to the normal configuration of the column and the sample outlet in the casing of a gas chromatograph unit 51, which prevents standardization of gas chromatograph units and increases the cost. In usage also, an additional plan area (table-top or floor space) is necessary for the mass spectrometer unit 52 besides that for the casing of the gas chromatograph unit 51, whereas a normal detector does not require such an additional area because it is mounted on the top of the casing as described above. The irregular configuration of a conventional gas chromatograph system with a mass spectrometer unit thus prevents consistent arrangement of gas chromatograph units and lowers the efficiency of space utility in normally narrow laboratories or the like.

SUMMARY OF THE INVENTION

An object of the present invention is therefore to enable a standardization of the structure of gas chromatograph unit whether it is coupled with a normal detector or it is coupled with a mass spectrometer unit. The standardization provides simplified manufacturing and handling lines and considerably reduces the manufacturing cost. Another object of the present invention is to provide a gas chromatograph/mass spectrometer system that requires a smaller plan area (table-top or floor space) when it is installed or when it is used.

The above and other objects are realized by a gas chromatograph/mass spectrometer system of the present invention that uses a suitably modified and re-designed mass spectrometer, which is mounted on the top of the casing of a gas chromatograph unit.

In the system of the present invention, a sample gas outlet of the gas chromatograph unit is disposed in the top of the casing of the gas chromatograph unit, whereas a sample gas inlet of the mass spectrometer unit is disposed in the bottom of the mass spectrometer unit. When the mass spectrometer unit is mounted on the top of the casing of the gas chromatograph unit, the sample gas outlet is connected to the sample gas inlet of the mass spectrometer unit, forming the minimum path between the column in the gas chromatograph unit and the mass spectrometer unit. When a gas chromatograph analysis is conducted, a constituent of the sample gas separated by the column placed in an oven (which is housed in the casing of the gas chromatograph unit) flows through the minimized path and comes into the mass spectrometer unit for a mass spectrometric analysis, which prevents dispersion of the constituent in the carrier gas and maintains the sharp peaks of the chromatogram.

Since, in the gas chromatograph/mass spectrometer system of the present invention, the mass spectrometer unit is mounted on the top of the gas chromatograph unit, the configuration of the sample gas outlet, the column and other components of the gas chromatograph unit inside of the casing can be set in common with that of a conventional gas chromatograph unit coupled with a normal detector. This enables the structure of the gas chromatograph unit being substantially identical with that of the conventional gas chromatograph system with a normal detector, which simplifies the manufacturing and handling lines and reduces the manufacturing cost considerably. Since the plan area (table-top or floor space) needed to install the mass spectrometer unit is mostly comprised in the installation area of the gas chromatograph unit, the gas chromatograph/mass spectrometer system of the present invention can be installed even in narrow laboratories. The small installation area allows other analytical apparatuses being installed in close neighbors, which enables a prompt analyses of a rapidly degradable sample in various aspects.

In a preferred application of the present invention, terminals for the power line, control and detection signal lines, and other necessary electrical lines of both the gas chromatograph unit and the mass spectrometer unit may be arranged at the corresponding positions of the upper and the lower units. These terminals are designed to be respectively aligned and connected with each other, manually or automatically, when the mass spectrometer unit is mounted on the top of the casing of the gas chromatograph unit. This structure allows a single power source unit and a single operation panel (which usually includes a keyboard and a display) to be disposed in either one of the units. The user can control the whole system including both the gas chromatograph unit and the mass spectrometer unit and can analyze data through the operation of the control panel provided to either one of the units.

The foregoing configuration of the gas chromatograph unit and the mass spectrometer unit allows the following structure of the mass spectrometer unit. The casing of the mass spectrometer unit is composed of a flat base plate and an air-tight enclosing concave cover. All the openings of the mass spectrometer unit, such as the sample gas inlet, electricity conduit, etc., necessary to connect to the gas chromatograph unit are made in the base plate, and there is no opening in the top enclosing cover. Thus the enclosing cover is easy to manufacture and the manufacturing cost is reduced. Another advantage of the structure is that the maintenance of the components inside of the mass spectrometer unit is facilitated because they stand open on the base plate and are easily accessible when the enclosing cover is removed. The casing of conventional mass spectrometers, on the other hand, is composed of a box housing having several openings and a flat cover. In this case, the box housing is difficult to manufacture and the maintenance of the inside of the mass spectrometer unit is troublesome because the components are surrounded by the walls of the box housing.

Other features of the present invention is detailed in the following description of the preferred embodiment.

BRIEF DESCRIPTION OF THE DRAWINGS

FIG. 1A is a side view of a gas chromatograph/mass spectrometer system embodying the present invention add FIG. 1B is a cross sectional view of the gas chromatograph/mass spectrometer system;

DETAILED DESCRIPTION OF A PREFERRED EMBODIMENT

Figure 2:
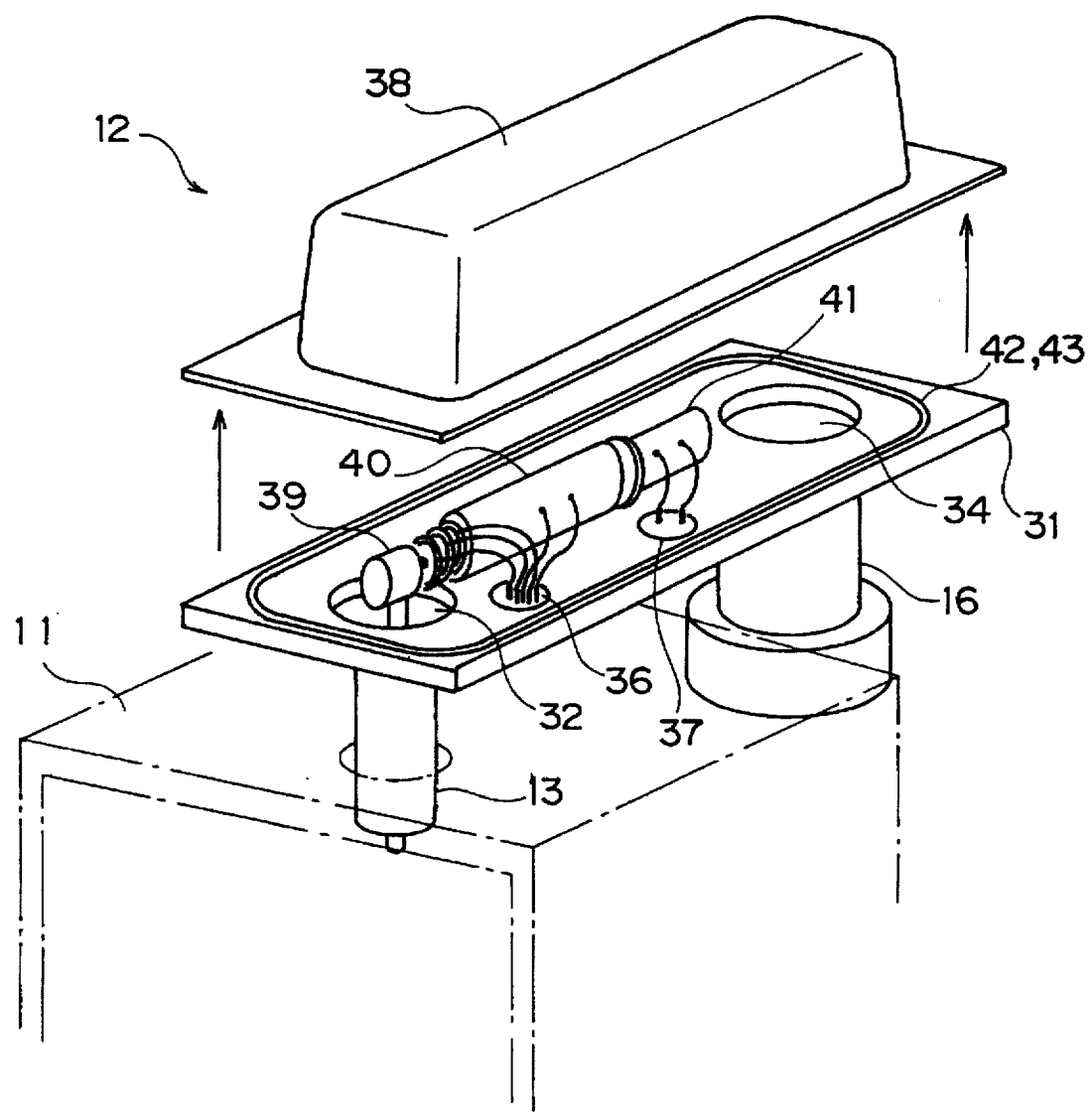
FIG. 2 is a perspective view of the mass spectrometer unit of the gas chromatograph/mass spectrometer system of the embodiment with the enclosing cover raised.

A gas chromatograph/mass spectrometer embodying the present invention is described with reference to FIGS. 1A, 1B and 2. A gas chromatograph/mass spectrometer system 10 of the present embodiment includes a gas chromatograph unit 11 and a mass spectrometer unit 12. As shown in FIG. 1B, the gas chromatograph unit 11 includes a capillary column 20 (or sometimes a plurality of columns), a heater 22 and a fan 23 for heating the capillary column 20, and a thermal insulation member 24 surrounding the heater 22, fan 23 and column 20. Thus the inner space of the casing of the gas chromatograph unit 11 is mostly occupied by an oven surrounded by the thermal insulation member 24. A small electric circuit rack 25 including a power source unit and a control unit for the gas chromatograph unit 11 and the mass spectrometer unit 12 is also provided in the casing of the gas chromatograph unit 11.

Referring to FIG. 1A, the mass spectrometer unit 12 includes an ion source 39, a quadrupole unit 40, and an ion detector 41 (hereinafter collectively referred to as mass spectrometer members). The mass spectrometer unit 12 is mounted on the top of the gas chromatograph unit 11, and they are connected to each other via a sample flow conduit 13 passing through the top of the casing of the gas chromatograph unit 11 and the bottom of the mass spectrometer unit 12. A vacuum pump (a turbo-molecular pump, for example) 15 is fixed via an exhaust pipe 16 to the bottom of the mass spectrometer unit 12 at the end opposite to the sample flow conduit 13. A gas sample inlet 18 for providing a sample gas to the chromatographic column 20 is placed in the top face of the gas chromatograph unit 11, and an operation panel 17 is provided in a side face of the gas chromatograph unit 11. Detailed structure of the mass spectrometer unit 12 will be described later.

Figure 3:
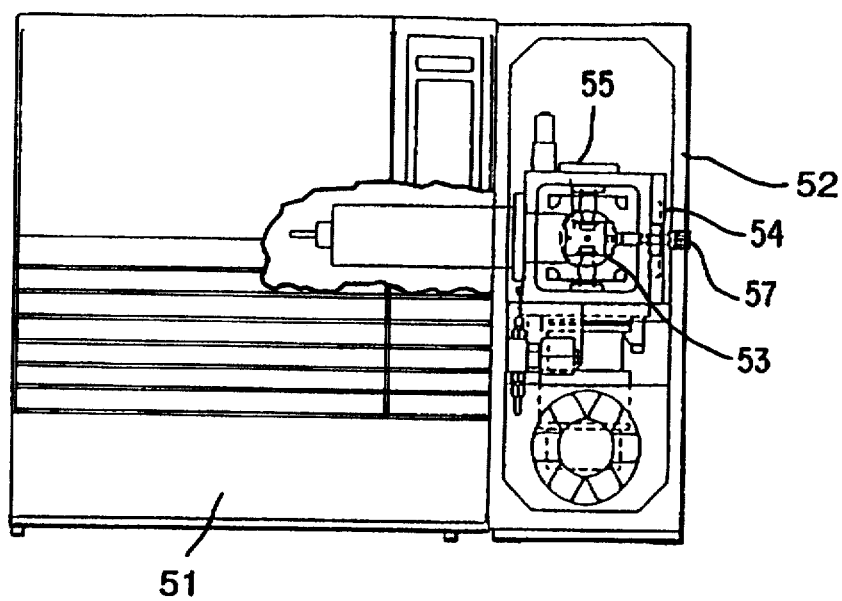
FIG. 3 is a side view of a conventional gas chromatograph/mass spectrometer with an inside view of the mass spectrometer unit.

In a conventional gas chromatograph/mass spectrometer system with the mass spectrometer unit 52 attached aside (see FIG. 3), the sample gas outlet should be disposed in the side face of the casing in order to minimize the travel distance of the gas effluent from the column to the mass spectrometer unit and to avoid dispersion in the travel. This necessitates a different design of the gas chromatograph unit 51 from that of a conventional gas chromatograph unit coupled with a normal detector. In the gas chromatograph/mass spectrometer system 10 of the present embodiment having the structure described above, however, a gas chromatograph unit designed for a conventional gas chromatograph system can be used.

Since the mass spectrometer unit 12 is mounted on the top of the gas chromatograph unit 11, no additional table-top or floor space is substantially needed besides that for the gas chromatograph unit 11. This provides an efficient use of a narrow table-top or laboratory floor, and enables other analytical apparatuses to be placed in close neighbors.

Another feature of the gas chromatograph/mass spectrometer system of the present embodiment is that the casing of the mass spectrometer unit 12 is composed of a planar base plate 31 and a bathtub-shaped enclosing cover 38, as shown in FIG. 2. The mass spectrometer members (the ion source 39, the quadrupole unit 40, the ion detector 41, etc.) are fixed on the base plate 31 and all the openings are formed in the base plate 31. In particular, the sample gas inlet 32 is formed in the base plate 31 immediately below the ion source 39. The vacuum port 34 is formed in a vacant space of the base plate 31. The sample gas inlet 32 connects with the sample flow conduit 13, and the vacuum port 34 with the exhaust pipe 16. Electricity conduits 36 and 37 are formed in the vicinity of the quadrupole unit 40 and the ion detector 41, wherein a feed-through unit with multiple conducting pins is fixed air-tightly in every electricity conduit 36 and 37. Driving voltages to the ion source 39, an ion lens, the quadrupole unit 40, etc. are applied via the feed-through unit in the electricity conduit 36, whereas detection signal from the ion detector 41 is sent to the control unit in the gas chromatograph unit 11 via the feed-through unit of the other electricity conduit 37. Thus the operation of the whole gas chromatograph/mass spectrometer system 10 including the gas chromatograph unit 11 and the mass spectrometer unit 12 can be done solely on the operation panel 17.

The control unit (and/or the power source unit) for the mass spectrometer unit 12 may be provided separately from that for the gas chromatograph unit 11: it may be placed near the top of the casing of the gas chromatograph unit or it can be attached to the casing of the mass spectrometer unit 12.

A groove 42 is formed along the ends of the base plate 31, and an O-ring 43 is fitted in the groove 42, whereby the enclosing cover 38, is air-tightly sealed to the base plate 31.

Figure 4:
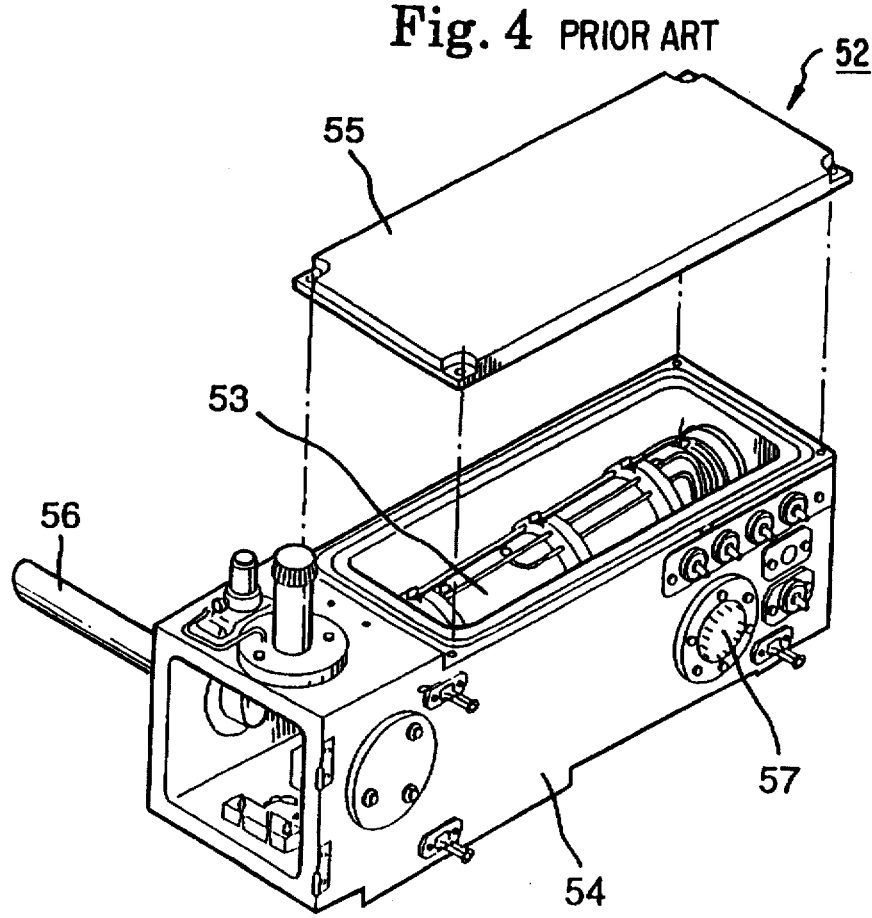
FIG. 4 is a perspective view of a mass spectrometer unit of a conventional gas chromatograph/mass spectrometer system with the flat cover raised.
Figure 5:
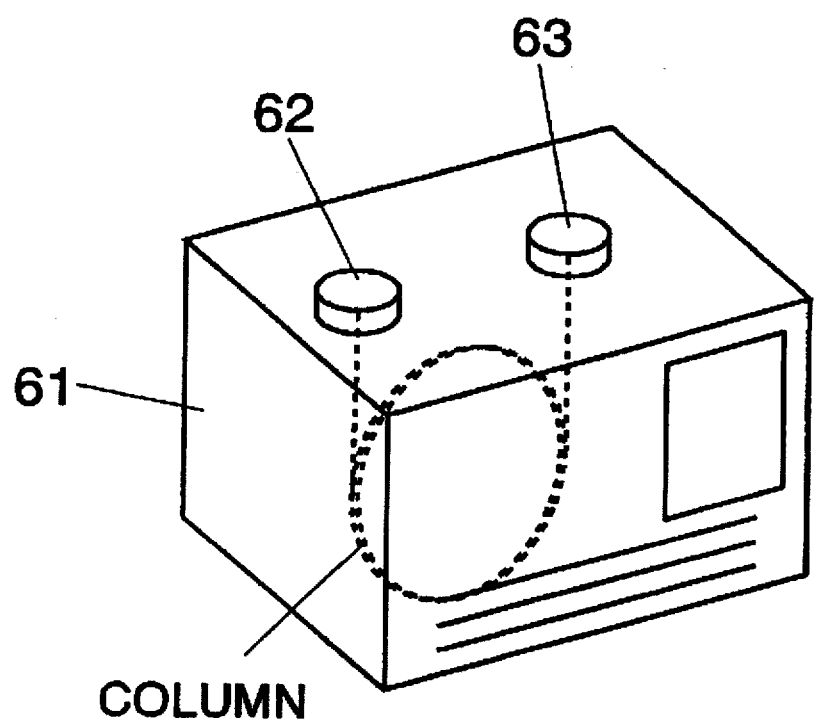
FIG. 5 is a perspective view of a casing of gas chromatograph unit.

In a mass spectrometer unit of a conventional gas chromatograph/mass spectrometer system as shown in FIG. 4, mass spectrometer members are placed in a casing composed of a box housing 54 and a flat cover 55. The openings such as a sample gas inlet 56, an electricity conduit 57, and a vacuum port (not shown in the drawing but provided in the bottom face of the box housing 54) are arranged in several face of the box housing 54. Thus the box housing is rather complicated and it requires time- and labor-consuming process to manufacture it, which naturally causes a high manufacturing cost. Another problem about the conventional mass spectrometer casing is the difficulty in the maintenance of the mass spectrometer members 53 because they are accommodated in the narrow box housing 54.

In the mass spectrometer unit 12 of the present embodiment, on the other hand, the spectrometer members are placed on the flat base plate, and all the openings such as the electricity conduits, 36 and 37, the vacuum port 34, etc. are formed in the base plate 31. Thus the enclosing cover 38 needs no openings, which thereby can be easily manufactured. When the enclosing dome or inverted bathtub-shaped cover 38 is removed, the mass spectrometer members stand open and are accessed freely from any direction, which facilitates the maintenance.

What is claimed is:

1. A gas chromatograph/mass spectrometer system comprising:

a gas chromatograph unit for sample gas analysis contained in a first casing including an oven for heating a gas chromatographic column; and a mass spectrometer unit contained in a second casing mounted on a top of the first casing to economize usage of available table top or floor space, where said mass spectrometer unit is designed with a base plate for supporting thereon internal components of said mass spectrometer unit so that said sample gas passing through from said gas chromatograph unit to said mass spectrometer unit flows through a minimum path, thereby yielding sharp chromatograph peaks by a resultant reduced amount of dispersion effected within said sample gas, and where said mass spectrometer has a removable top cover for allowing easy access, replacement and maintenance of said internal components.

2. The gas chromatograph/mass spectrometer according to claim 1, wherein a gas outlet and electricity terminal or terminals are disposed in a top face of the gas chromatograph unit and a gas inlet and an electricity terminal or terminals corresponding to said electricity terminal or terminals of the gas chromatograph unit are disposed in a bottom face of the mass spectrometer unit.

3. The gas chromatograph/mass spectrometer system according to claim 2, wherein the mass spectrometer unit has a second casing composed of a flat base plate and an enclosing concave cover wherein all sample gas supply and electrical line or conduit openings necessary to connect the gas chromatograph unit and the mass spectrometer unit are formed in the flat base plate and the enclosing concave cover has no openings.

4. The gas chromatograph/mass spectrometer according to claim 3, wherein a single power source and a single control unit for both the gas chromatograph unit and the mass spectrometer unit are provided in either one of the gas chromatograph unit and the mass spectrometer unit.

5. The gas chromatograph/mass spectrometer according to claim 4, wherein the mass spectrometer unit comprises a quadrupole mass analyzer.

6. The gas chromatograph/mass spectrometer system according to claim 1, wherein the mass spectrometer unit has a second casing composed of a flat base plate and an enclosing concave cover, where all openings necessary to connect the gas chromatograph unit and the mass spectrometer unit are formed in the flat base plate and the enclosing concave cover has no openings.

7. The gas chromatograph/mass spectrometer according to claim 6, wherein a single power source and a single control unit for both the gas chromatograph unit and the mass spectrometer unit are provided in the first casing.

8. The gas chromatograph/mass spectrometer according to claim 7, wherein the mass spectrometer unit comprises a quadrupole mass analyzer.

* * * * *